(12) United States Patent
Lu et al.

(10) Patent No.: US 11,207,008 B2
(45) Date of Patent: Dec. 28, 2021

(54) METHOD AND SYSTEM FOR DETECTING THE OXYGEN SATURATION WITHIN THE BLOOD

(71) Applicant: VITA-COURSE TECHNOLOGIES (HAINAN) CO., LTD., Hainan (CN)

(72) Inventors: Ying Lu, Haikou (CN); Chuanmin Wei, Haikou (CN); Jiwei Zhao, Haikou (CN); Heng Peng, Haikou (CN); Ziming Deng, Haikou (CN); Zijian Huang, Haikou (CN); Zhiyong Wang, Haikou (CN)

(73) Assignee: VITA-COURSE TECHNOLOGIES (HAINAN) CO., LTD., Haikou (CN)

( * ) Notice: Subject to any disclaimer, the term of this patent is extended or adjusted under 35 U.S.C. 154(b) by 0 days.

(21) Appl. No.: 16/492,541

(22) PCT Filed: Nov. 20, 2017

(86) PCT No.: PCT/CN2017/111938
§ 371 (c)(1),
(2) Date: Sep. 9, 2019

(87) PCT Pub. No.: WO2019/019491
PCT Pub. Date: Jan. 31, 2019

(65) Prior Publication Data
US 2020/0375512 A1    Dec. 3, 2020

Related U.S. Application Data

(63) Continuation-in-part of application No. PCT/CN2017/094762, filed on Jul. 27, 2017.

(51) Int. Cl.
*A61B 5/1455* (2006.01)
*G16H 40/67* (2018.01)
(Continued)

(52) U.S. Cl.
CPC ........ *A61B 5/14551* (2013.01); *A61B 5/0022* (2013.01); *A61B 5/021* (2013.01);
(Continued)

(58) Field of Classification Search
CPC .............. A61B 5/1455; A61B 5/14551; A61B 5/14552; A61B 5/14532; A61B 5/6802;
(Continued)

(56) References Cited

U.S. PATENT DOCUMENTS 5,725,480 A * 3/1998 Oosta .................... A61B 5/1455
600/310
8,346,327 B2 * 1/2013 Campbell .......... A61B 5/14551
600/310

(Continued)

FOREIGN PATENT DOCUMENTS

CN    101032395 A    9/2007
CN    101980228 A    2/2011
(Continued)

OTHER PUBLICATIONS

International Search Report in International Application No. PCT/CN2017/111938 dated Apr. 28, 2018, 16 pages.
(Continued)

*Primary Examiner* — Chu Chuan Liu
(74) *Attorney, Agent, or Firm* — Metis IP LLC

(57) ABSTRACT

The present disclosure provides a system and method for analyzing a physiological parameter of a vital sign signal. The method may include acquiring a vital sign signal, storing data, computing and analyzing, processing, and outputting a result. The system may compute and analyze the physiological parameter of the vital sign signal, especially a blood oxygen saturation, via a plurality of algorithms, judge or process the computation result, and output the judgment result.

20 Claims, 6 Drawing Sheets

(51) Int. Cl.
  *G16H 50/30* (2018.01)
  *G16H 50/70* (2018.01)
  *G16H 50/20* (2018.01)
  *A61B 5/021* (2006.01)
  *A61B 5/00* (2006.01)
  *G16H 10/60* (2018.01)
  *A61B 5/318* (2021.01)
  *A61B 5/024* (2006.01)

(52) U.S. Cl.
  CPC ........ *A61B 5/02125* (2013.01); *A61B 5/6802* (2013.01); *A61B 5/726* (2013.01); *A61B 5/7257* (2013.01); *A61B 5/7271* (2013.01); *A61B 5/7275* (2013.01); *A61B 5/7475* (2013.01); *G16H 10/60* (2018.01); *G16H 40/67* (2018.01); *G16H 50/20* (2018.01); *G16H 50/30* (2018.01); *G16H 50/70* (2018.01); *A61B 5/02416* (2013.01); *A61B 5/318* (2021.01)

(58) Field of Classification Search
  CPC ......... A61B 5/7475; A61B 5/726; A61B 5/02; A61B 5/02125; A61B 5/7275; A61B 5/7257; A61B 5/7271; A61B 5/0022; A61B 5/021; A61B 5/318; A61B 5/02416; A61B 5/145; A61B 5/0205
  See application file for complete search history.

(56) References Cited

U.S. PATENT DOCUMENTS

| | | | |
|---|---|---|---|
| 9,554,735 B2* | 1/2017 | Rebec | A61B 5/1455 |
| 2008/0039731 A1 | 2/2008 | Mccombie et al. | |
| 2011/0124982 A1 | 5/2011 | Pipke | |
| 2011/0196244 A1 | 8/2011 | Ribas Ripoll et al. | |
| 2012/0136261 A1 | 5/2012 | Sethi et al. | |
| 2013/0012823 A1 | 1/2013 | Ripoll et al. | |
| 2013/0116580 A1 | 5/2013 | Liu et al. | |
| 2014/0066788 A1 | 3/2014 | Mukkamala et al. | |
| 2015/0313486 A1 | 11/2015 | Mestha et al. | |
| 2015/0374244 A1 | 12/2015 | Yoo et al. | |
| 2015/0377909 A1 | 12/2015 | Cavet et al. | |
| 2016/0045119 A1 | 2/2016 | David et al. | |
| 2016/0135755 A1 | 5/2016 | Lu et al. | |
| 2016/0192887 A1 | 7/2016 | Sun et al. | |
| 2018/0160905 A1 | 6/2018 | Wang et al. | |

FOREIGN PATENT DOCUMENTS

| | | |
|---|---|---|
| CN | 102186411 A | 9/2011 |
| CN | 102270264 A | 12/2011 |
| CN | 102397064 A | 4/2012 |
| CN | 102908130 A | 2/2013 |
| CN | 102930163 A | 2/2013 |
| CN | 103637787 A | 3/2014 |
| CN | 104323764 A | 2/2015 |
| CN | 104434311 A | 3/2015 |
| CN | 104720773 A | 6/2015 |
| CN | 105455797 A | 4/2016 |
| CN | 106725376 A | 5/2017 |
| WO | 2013109188 A1 | 7/2013 |
| WO | 2014063518 A1 | 5/2014 |
| WO | 2016155348 A1 | 10/2016 |
| WO | 2016187847 A1 | 12/2016 |
| WO | 2017005016 A1 | 1/2019 |

OTHER PUBLICATIONS

International Search Report in International Application No. PCT/CN2017/094762 dated May 3, 2018, 4 pages.
Written Opinion in International Application No. PCT/CN2017/094762 dated May 3, 2018, 4 pages.
Written Opinion in International Application No. PCT/CN2017/111938 dated Apr. 28, 2018, 6 pages.
International Search Report in PCT/CN2017/111938 dated Apr. 28, 2018, 16 pages.
Written Opinion in PCT/CN2017/111938 dated Apr. 28, 2018, 6 pages.
International Search Report in PCT/CN2017/076702 dated Jun. 7, 2017, 5 pages.
Written Opinion in PCT/CN2017/076702 dated Jun. 7, 2017, 5 pages.
First Office Action in Chinese Application No. 201780020746.0 dated Sep. 15, 2020, 20 pages.
The Extended European Search Report in European Application No. 17773043.9 dated Mar. 21, 2019, 8 pages.

* cited by examiner

METHOD AND SYSTEM FOR DETECTING THE OXYGEN SATURATION WITHIN THE BLOOD

CROSS-REFERENCE TO RELATED APPLICATION

This application is a national phase entry under 35 U.S.C. § 371 of PCT Application No. PCT/CN2017/111938 entitled "METHOD AND SYSTEM FOR DETECTING THE OXYGEN SATURATION WITHIN THE BLOOD," filed on Nov. 20, 2017, which claims priority of PCT Application No. PCT/CN2017/094762, entitled "SYSTEMS AND METHODS FOR DETERMINING BLOOD PRESSURE OF A SUBJECT," filed on Jul. 27, 2017, the contents of each of which are hereby incorporated by reference.

TECHNICAL FIELD

The present disclosure generally relates to a method and system for acquiring, processing, extracting, and analyzing a vital sign signal, and more particularly, to a method and system for computing and correcting a physiological parameter of a vital sign signal.

BACKGROUND

Photoplethysmography (PPG) is a non-invasive method for detecting changes of blood volume in an organism via a photoelectric method. Basic physiological parameters, for example, the heart rate, the oxygen saturation with the blood (also referred to as the blood oxygen saturation), the respiratory rate, the blood pressure, etc., of a human body may be obtained via PPG. A PPG signal may include a wealth of physiological and pathological information, and many diseases, especially heart diseases, may clinically make the pulse change. A traditional blood oxygen detecting device may use red light, infrared light, near-infrared light, etc., to obtain relationships between the blood oxygen saturation and light intensity at different wavelengths according to the Lambert-Beer law, because different substances in the blood may have different absorptivities at different wavelengths.

The blood oxygen detecting device based on an optical non-invasive indirect measurement technique has been developed since the 19th century. Suitable for different measurement scenarios, the blood oxygen detecting device, including the transmissive device and the reflective device, has been developed. Manufacturers and researchers have proposed different solutions aiming at different measurement problems, such as poor perfusion, motion interference, error caused by different skin colors and/or tissues. However, the detecting accuracy is still limited by the above measurement problems. Therefore, it is desirable to develop a method and system for correcting various physiological parameters (e.g., for the computation of the blood oxygen saturation) under different measurement scenarios for different measurement problems in a unified framework.

SUMMARY

The present disclosure discloses a method. The method may include: acquiring a vital sign signal; preprocessing the acquired vital sign signal; establishing a group of computing models of the physiological parameter based on one or more different populations; establishing a decision model to determine a plurality of populations to which the vital sign signal corresponds; computing a weight of the vital sign signal for each of the plurality of populations to which the vital sign signal corresponds; and correcting a value of the physiological parameter of the vital sign signal based on the weights.

According to some embodiments of the present disclosure, the vital sign signal may include a pulse wave signal.

According to some embodiments of the present disclosure, the vital sign signal may include information of blood oxygen.

According to some embodiments of the present disclosure, the physiological parameter may include blood oxygen saturation.

According to some embodiments of the present disclosure, the one or more different populations may include at least populations with different skin colors.

According to some embodiments of the present disclosure, the one or more different populations may include at least a population with a characteristic of poor perfusion.

According to some embodiments of the present disclosure, the one or more different populations may include at least a population with a characteristic of motion interference.

According to some embodiments of the present disclosure, the group of computing models of the physiological parameter may be generated by performing at least one of a time domain transformation, a frequency domain transformation, or a time-frequency domain transformation on the vital sign signal.

According to some embodiments of the present disclosure, the decision model may be a multi-classification model.

According to some embodiments of the present disclosure, the computation of the weights is based on a distance between the vital sign signal and each of the plurality of populations to which the vital sign signal corresponds.

The present disclosure may also disclose a system. The system may include a storage device, and the storage device may be configured to execute a plurality of sets of instructions for noise detection of a vital sign signal, and execute operations of: acquiring a vital sign signal; preprocessing the acquired vital sign signal; establishing a group of computing models based on a physiological parameter based on one or more different populations; establishing a decision model to determine a plurality of populations to which the sign signal corresponds; computing a weight of the vital sign signal in each of the plurality of populations to which the vital sign signal belongs; and correcting a value of the physiological parameter of the vital sign signal based on the weight.

According to some embodiments of the present disclosure, the vital sign signal may include a pulse wave signal.

According to some embodiments of the present disclosure, the vital sign signal may include information of blood oxygen.

According to some embodiments of the present disclosure, the physiological parameter may include blood oxygen saturation.

According to some embodiments of the present disclosure, the one or more different populations may include at least populations with different skin colors.

According to some embodiments of the present disclosure, the one or more different populations may include at least a population with a characteristic of poor perfusion.

According to some embodiments of the present disclosure, the one or more different populations may include at least a population with a characteristic of motion interference.

According to some embodiments of the present disclosure, the group of computing models of the physiological parameter may be generated by performing at least one of a time domain transformation, a frequency domain transformation, or a time-frequency domain transformation on the vital sign signal.

According to some embodiments of the present disclosure, the decision model may be a multi-classification model.

According to some embodiments of the present disclosure, the computation of the weights is based on a distance from the vital sign signal to each of the plurality of populations to which the vital sign signal corresponds.

DETAILED DESCRIPTION

Figure 1:
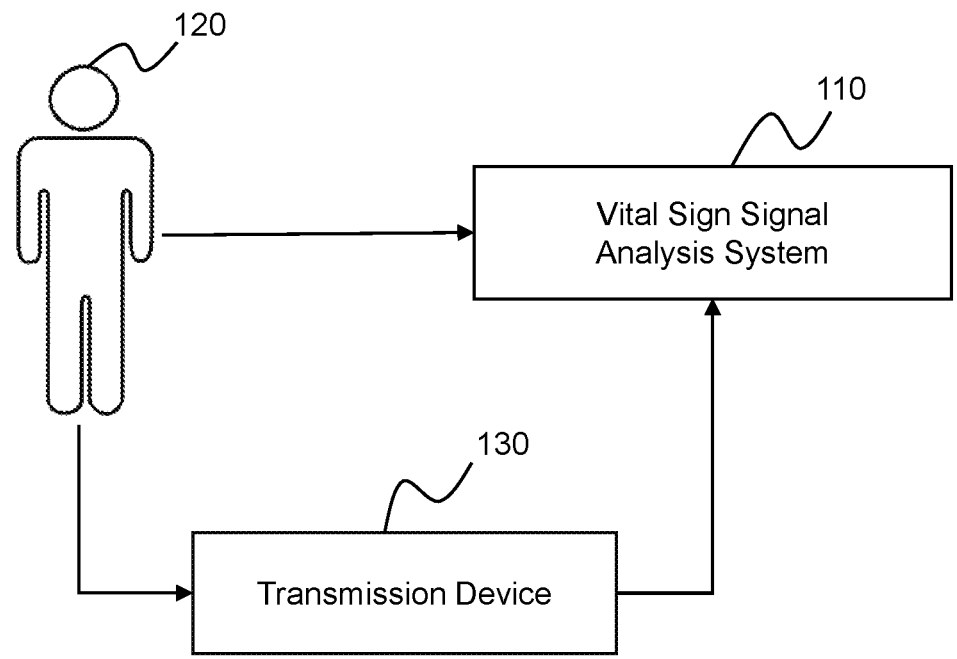
FIG. 1 is a schematic diagram illustrating an application scenario of a vital sign signal analysis system according to some embodiments of the present disclosure.

The system for analyzing a vital sign signal related to the description may be used for a plurality of fields which may include, but are not limited to guardianship (including but not limited to the guardianship for elderly people, the guardianship for middle-aged people, the guardianship for young people, and the guardianship for infants, etc.), medical diagnosis (including but not limited to electrocardio diagnosis, pulse diagnosis, blood pressure diagnosis, blood oxygen diagnosis, etc.), motion monitor (including but not limited to long-distance race, middle and short distance race, sprint, cycling, canoeing, archery, horse riding, swimming, climbing, etc.), hospital care (including but not limited to severe patient monitoring, genetic patient monitoring, emergency patient monitoring, etc.), pet care (critical cases pet care, newborn pet care, home pet care, etc.), or the like.

The vital sign signal analysis system may collect one or more vital sign signals of a living body including physical and chemical information, such as signals related to electrocardio, pulse, blood pressure, blood oxygen content, heart rate, body temperature, heart rate variability (HRV), blood pressure variability (BPV), brain waves, ultra-low frequency waves emitted by a human body, breathing, musculoskeletal status, blood glucose, blood lipids, haemoconcentration, platelet content, height, weight, or the like. The vital sign signal analysis system may include a storage device. The storage device may be configured to execute a plurality of sets of instructions for noise detection of a vital sign signal, and execute operations of: acquiring a vital sign signal; preprocessing the acquired vital sign signal; establishing a group of computing models of a physiological parameter based on one or more different populations; establishing a decision model to determine a plurality of populations to which the vital sign signal corresponds; computing a weight of the vital sign signal for each of the plurality of populations to which the vital sign signal corresponds; and correcting a value of the physiological parameter of the vital sign signal based on the weights. An output module may be configured to output the result of analysis and computation. The analysis system may correct various physiological parameters under different measurement scenarios and measurement problems (e.g., in the computation of blood oxygen saturation) using a unified framework. The system may be conveniently applied to portable devices or wearable devices. The system may monitor the vital sign signal of a living body continuously in a real-time (or non-real-time) manner, and transmit a monitoring result to an external device (including but not limited to a storage device or cloud server). For example, the system may monitor the vital sign signal of a user continuously in a random period, for example, several minutes, hours, days, or months, or may continuously regularly monitor the vital sign signal of a user. The system may display a condition of the vital sign signal of a monitored living body, such as pulses, blood pressure, content of the blood oxygen, etc., and provide physiological information data to a third party, for example, a hospital, a nursing organization, or related people. For example, a user may use the system at home. The system may provide the monitored vital sign signal and the physiological information data to a remote hospital, a nursing organization, a related person, or the like. A part of or all of the user's vital sign signals or the physiological information data may also be stored in a local or remote storage device. The transmission mode of the physiological information data may be wired or wireless. The system may detect noise in the acquired vital sign signal effectively, and make corresponding matching and calibration (it may make it easy to implement this system on a portable device or a wearable device). Specifically, the analysis system may monitor the vital sign signal of a living body continuously in a real-time (or non-real-time) manner, and transmit the monitored result to the external device (including but not limited to a storage device or cloud server). The analysis system may output and display the monitored vital sign signals of the living body, such as the electrocardio, the pulse, the blood pressure, the concentration of the blood oxygen, etc., and remotely provide these vital sign signals to a third party, such as a hospital, a nursing organization, related people, or the like. All the above described transmission process of the vital sign signals may be wired or wireless.

The above description about the application may be provided for illustration purposes, and should not be considered as the only embodiment. Obviously, for persons having ordinary skills in the art, the application of the above method and system may be modified or altered in forms and details under the teaching of the basic principle of the analysis method and system of the vital sign signal. However, those modifications and alterations are within the scope of the above description.

In order to describe technical solutions in the embodiments of the present invention more clearly, attached drawings required for describing the embodiments may be briefly introduced below, and it is apparent that the drawings in the following description are merely some embodiments of the present disclosure, for persons having ordinary skills in the art, the drawings can be used to other similar scenarios according to these drawings without making creative efforts.

Unless stated otherwise or obvious from the context, the same reference numeral in the drawings refers to the same structure and operation.

As used in the disclosure and the appending claims, the singular forms "a," "an," and "the" include plural referents unless the content clearly dictates otherwise. In general, the terms "comprise" and "include" merely prompt to include steps and elements that have been clearly identified, and these steps and elements do not constitute an exclusive listing. The methods or devices may also include other steps or elements.

FIG. 1 is a schematic diagram illustrating an application scenario of the vital sign signal analysis system according to some embodiments of the present disclosure. The application scenario may include but is not limited to a vital sign signal analysis system 110, a living body 120, and a transmission device 130. The vital sign signal analysis system 110 may be configured to extract, receive, obtain, analyze, and/or process the vital sign signals from the living body 120. The living body 120 may include but is not limited to a human body, and is not limited to a single living body. The vital sign signal may include but is not limited to physical and chemical information, such as electrocardio, pulse, blood pressure, blood oxygen, heart rate, body temperature, HRV, BPV, brain waves, body waves, ultra-low frequency emitted by a human body, breathing, musculoskeletal conditions, blood glucose, blood lipids, haemoconcentration, platelet content, height, weight, or the like. The transmission device 130 may include but is not limited to a processor, a sensor, an embedded device based on a single chip or Advanced RISC Machine (ARM), an analyzer, a detector, and other electronic, mechanical, physical, and/or chemical devices. The transmission manner may include but is not limited to transmission through radar, infrared, Bluetooth™, electric wire, optical fiber, and/or other wired or wireless manner. The transmitted information may be analogue or digital, real-time or non-real-time. The device may be configured for a specific living body, or a group of living bodies, one or more types of living body. The device may also include a central database or a cloud server. The vital sign signal analysis system 110 may obtain the vital sign signal directly or indirectly. The acquired vital sign signal may be directly transmitted to the vital sign signal analysis system 110, or transmitted to the vital sign signal analysis system 110 via the transmission device 130. The device for acquiring the vital sign signal may include but is not limited to a heartbeat collection device, an electrocardiogram detector, a pulse wave detector, a brain wave detector, a blood pressure measuring device, a vital sign detection device, and/or a human respiratory detector, and may also include smart wearable devices and portable devices such as watches, headphones, eyeglasses, and accessories that have the functions of the above devices. In some embodiments, the vital sign signals of the human body may be acquired using smart clothes equipped with a sensor (e.g., a photoelectric sensor or a pressure sensor).

The description above about the application scenario of the vital sign signal analysis system is merely a specific embodiment provided for illustration purposes, and should not be considered as the only embodiment. Obviously, for persons having ordinary skills in the art, the application way of the vital sign signal analysis system may be modified or altered in forms and details under the teaching of the basic principle of the analyzing and system of the vital sign signal. However, those modifications and alterations are within the scope of the above description. For example, the information acquired from the living body 120 may be transmitted to the vital sign signal analysis system 110 directly, instead of transmitting via the transmission device 130. The vital sign signal analysis system 110 may also directly acquire a plurality of different types of vital sign signals from a plurality of living bodies 120 to process comprehensively. Those modifications and alterations are within the scope of the present disclosure.

Figure 2:
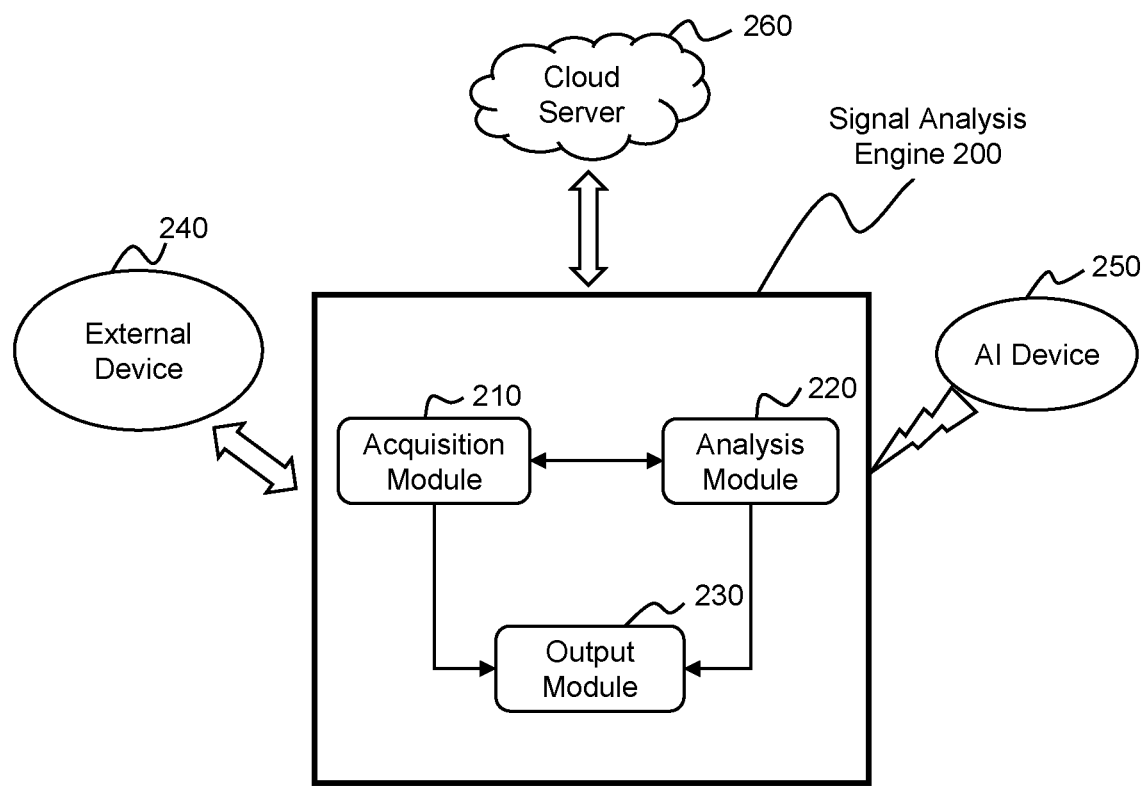
FIG. 2 is a schematic diagram illustrating a vital sign signal analysis system according to some embodiments of the present disclosure.

FIG. 2 is a schematic diagram illustrating a vital sign signal analysis system according to some embodiments of the present disclosure. The analysis system may include but is not limited to one or more signal analysis engines 200, one or more external devices 240, one or more AI devices 250, and a cloud server 260, etc. The signal analysis engine 200 may include but is not limited to an acquisition module 210, an analysis module 220 and an output module 230, etc. The acquisition module 210 may be mainly configured to acquire a vital sign signal through the vital sign signal analysis system. The acquisition module 210 may be realized using a photoelectric sensing method, or an electrode sensing method. The acquisition module 210 may obtain the vital sign signal via temperature sensing, humidity change, pressure change, photoelectric sensing, potential change of a body surface, voltage change, current change, or magnetic field change, etc. The acquisition module 210 may obtain various information, such as acoustics, optics, magnetism, and thermodynamics. The type of the information may include but is not limited to pulse information, heart rate information, electrocardio information, blood pressure information, blood oxygen information, respiration information, and/or other vital sign signals. For example, the acquisition module may obtain information about pulse waves. The information about pulse waves may include but is not limited to waveforms, time intervals, peaks, troughs, amplitude, etc., relating to the pulse waves. The acquisition module 210 may make full use of all kinds of devices, such as a local pulse wave acquisition device or a remote wireless pulse wave monitoring system, a medical pulse wave monitoring system, a household portable pulse wave monitoring device, a traditional pulse wave monitoring device, a portable smart wearable device (e.g., a smart watch or headset with such a function). According to the actual needs, the acquisition module 210 may acquire a complete vital sign signal or a part of the vital sign signal within a certain time interval, such as a window length of two seconds (2 s).

A calibration module may be integrated into the acquisition module 210. Alternatively or additionally, a standalone calibration module (not shown) may be set inside the signal analysis engine 200. The calibration module may be configured to adjust, optimize, and/or calibrate the acquired vital sign signals or remove interference caused by irrelevant error. The acquisition of vital sign signals may be influenced by a plurality of factors, which may affect the waveform, peak amplitude, and/or peak interval of the vital sign signals. For example, the vital sign signals of the same living body at different time points of a day may be different. The vital sign signals of the same living body under different life conditions (e.g., in a motion state or in a rest state, in a high-intensity working state or in a sleep state, in a joyful state or in an angry state) may also be different. The vital sign signals of the same living body may be different in the state of taking medicine or in the state of not taking medicine. Besides, the vital sign signals of different living bodies may be different in a same state. Therefore, a corresponding calibration module may be integrated into the acquisition module 210, or a corresponding calibration module (not shown in the figures) may be configured within the signal analysis engine 200, to adjust, optimize, calibrate, or remove the above error interference, and to obtain accurate vital sign signals. In addition, the acquisition module 210 may adjust different parameters for different living bodies, store the vital sign signals acquired from a same living body in the cloud server 260, which may enable the acquisition module 210 to have a self-adaptive function and form a database of individual vital sign signals of the same living body, to make the acquired vital sign signals more accurate. In addition, the photoelectric sensing may be influenced by luminous intensity, skin color, skin roughness, skin temperature, skin humidity, ambient temperature, ambient humidity, etc. Therefore, an environment adaptive module, such as a correction or a compensation module corresponding to environment influencing factors, may be integrated into the acquisition module 210. The above modifications, alterations, or changes of the vital sign signal analysis system are within the scope of the present disclosure.

The analysis module 220 may be mainly configured to compute, analyze, determine, and/or process the vital sign signal. The analysis module 220 may be centralized or distributed, may be local or remote. The computing process may be related to a specific computation, or a yes/no determination based on a threshold. The analyzing process may be performed in real-time or not. The computing process may be performed directly by the system or by an external computer program. The device(s) used during the computing process may be an internal device of the system or an external device. The processing process may be performed in real-time or not. The processing process may be performed directly by the system or by an external program connected thereto. The output module 230 may be configured to output the computed, analyzed, determined, and/or processed vital sign signals. The output information may be analog or digital. The output information may be a logical result of a yes/no determination and/or a processed vital sign signal. The output process may be performed in real-time or not. The output process may be performed directly by the system or by an external device connected thereto. The external device 240 may generally refer to one or more devices directly or indirectly associated with a module of the vital sign signal analysis system. The external device 240 may be local or remote. The external device 240 may be wired or wireless. For example, the external device 240 may be a light emitting diode (LED) screen or a liquid crystal display (LCD) screen configured to display vital sign signals, or may be a storage device, such as a hard disk, a floppy disk, or the like, configured to store the vital sign signals. The AI (artificial intelligence) device 250 may generally refer to hardware or software that has self-learning function using data. The AI device 250 may include but is not limited to a central processing unit (CPU), a graphics processing unit (GPU), a tensor processing unit (TPU), an application specific integrated circuit (ASIC), and/or hardware or software which may perform a supporting vector machine (SVM) algorithm, a logistic regression (LR) algorithm, a long short-term memory (LSTM) algorithm, a generative adversarial network (GAN) algorithm, a Monte Carlo tree search (MCTS) algorithm, a hidden Markov Model (HMM) algorithm, a random forests algorithm, a recursive cortical network (RCN) algorithm, or the like.

The cloud server 260 may be configured to store all the data involved in the operations of the vital sign signal analysis system. The cloud server 260 may also provide data calling support for various modules of the system in real-time or non-real-time. The cloud server 260 may serve as a cloud database of the vital sign signal analysis system.

The analysis module 220 may be connected to the acquisition module 210. The connection may be wired or wireless. The acquisition module 210 and the analysis module 220 may be connected to the output module 230. The connection may be wired or wireless. The acquisition module 210, the analysis module 220, and the output module 230 may be respectively connected to a power source, or may share one power source by two or three of the modules. The acquisition module 210, the analysis module 220, and the output module 230 may be respectively connected to an external device. The external devices may be connected to one or more modules. The connection may be wired or wireless. The signal analyzing engine 200 may be connected to the cloud server 260. The connection may be wired or wireless. The various modules and devices described above may be not essential, for those skilled in the art after having knowledge of the content and principles of the present disclosure, the system is susceptible to various modifications and changes in form and detail, the modules may be arbitrarily combined, or some modules may be added or removed as needed. And such modifications and variations are still within the spirit and scope of the present disclosure. For example, the acquisition module 210 and the output module 230 in FIG. 2 may be integrated into one module which may include the both functions of acquiring information and output information. The integrated module may be connected to the analysis module 220 via a wired or wireless manner. A corresponding storage device may be integrated into each of the modules, which may be configured for short-term cache of information data during operations of the system, or for long-term storage of information data. A corresponding standalone storage module may be set inside the signal analysis engine 200 to store the acquired, computed, analyzed, and/or processed vital sign signals. Those modifications and alterations are within the scope of the present disclosure.

The connections between modules, the connection between a module and an external device, and the connection between the system and the storage device or the cloud server in the vital sign signal analysis system are not limited to the above description. The above described connection may be used alone or in combination. All modules may be integrated together to realize functions of one or more modules via one device. The external devices may also be integrated on an implementation device of one or more modules, and a single or a plurality of modules may also be integrated on one or more external devices. The connections among modules of the vital sign signal analysis system, the connection between the module and the external device, and the connection between the system and the storage device or the cloud server may be wired or wireless. The wired connection may include but is not limited to connection via electric wire, optical fiber, and other wired connections. The wireless connection may include but is not limited to connection via Bluetooth or infrared and/or other wireless connection.

Figure 3:
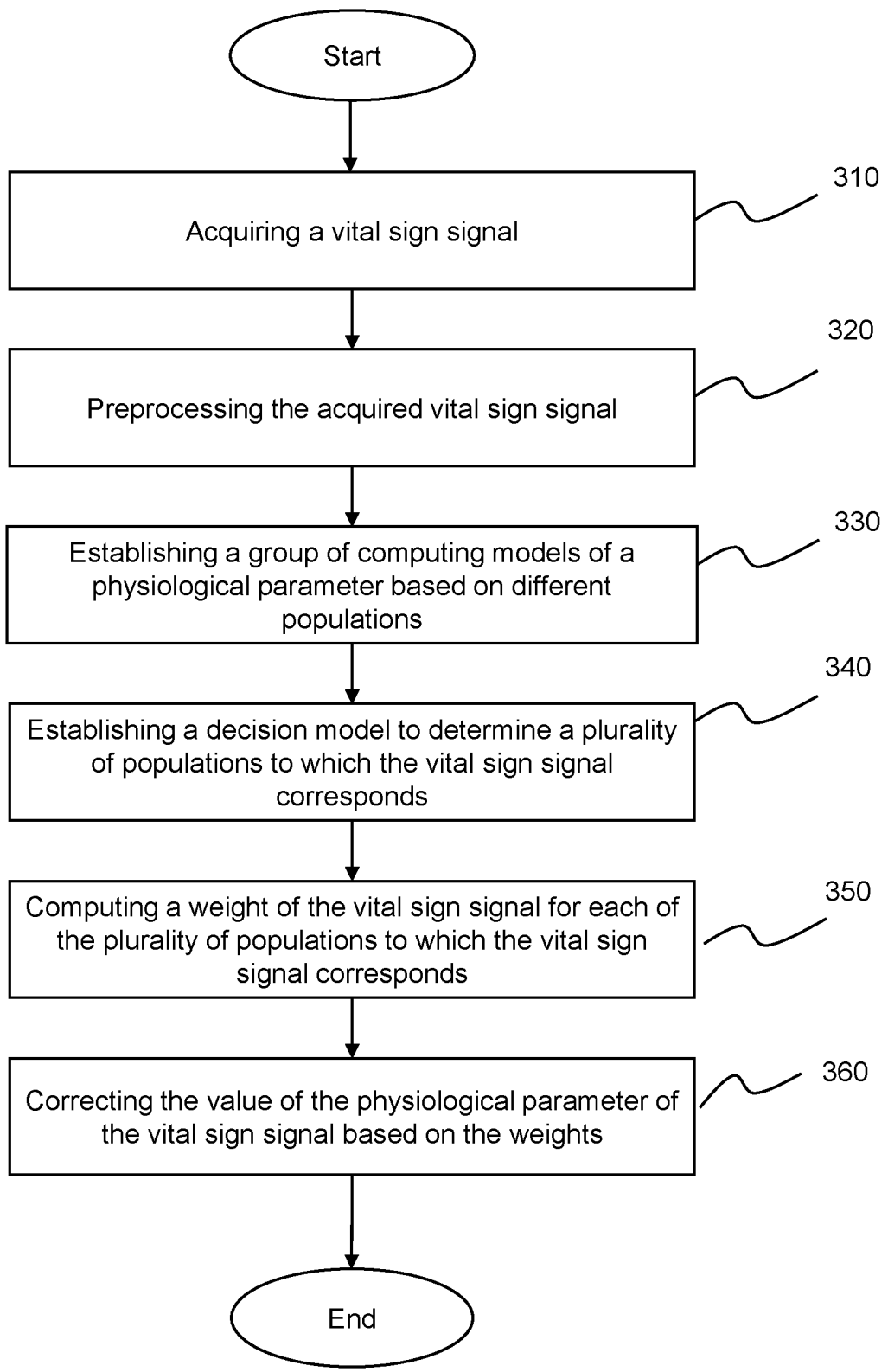
FIG. 3 is a flowchart illustrating an exemplary process of the operating of a vital sign signal analysis system according to some embodiments of the present disclosure.

FIG. 3 is a flowchart illustrating an exemplary process of the operating of a vital sign signal analysis system according to some embodiments of the present disclosure. The process may include following step: acquiring a vital sign signal in step 310. The data of the vital sign signal may be stored in the acquisition module in FIG. 2, stored in a corresponding storage device (not shown in the figure), or stored in the cloud server 260. The system may perform a next step directly without storing the acquired data of the vital sign signal. The vital sign signal may be preprocessed in step 320. The preprocessing step may be performed by the analysis module 220, or by another standalone preprocessing module (not shown). The information in the data may be optimized via the preprocessing of the data. The preprocessing may include but is not limited to correcting, altering, or removing noise information or redundant information from the data. Specifically, the pre-processing may include but is not limited to a low-pass filtering, a band-pass filtering, a wavelet transform filtering, a median filtering, a morphological filtering, a curve fitting, or the like. A part of identifiable noise of the data of the vital sign signal, such as baseline drift noise, may be removed via the pre-processing step. After the preprocessing, in step 330, a group of computing models of the physiological parameter based on different populations may be established to compute and analyze features related to the vital sign signal. Specifically, corresponding computing models of the physiological parameter may be established according to different populations of different vital sign signals. The step 330 may be executed by the analysis module 220. One or more built-in algorithms of the analysis module 220 may compute and/or analyze the features of the vital sign signal. After the computation and analysis, step 340 may be executed. In step 340, a decision model may be established to determine populations to which the vital sign signal corresponds. In step 350, a weight of the vital sign signal for each population to which the vital sign signal corresponds may be computed to determine the relative importance of the result parameter outputted by the corresponding computing model of the physiological parameter. Finally, in step 360, the physiological parameter of the vital sign signal may be modified based on the weights.

The methods and steps described herein may occur in any suitable order or simultaneously. In addition, individual step may be deleted from any of the methods without departing from the spirit and scope of the subject described herein. The aspects of any embodiments described above may be combined with any aspect of any of the other embodiments described to constitute further embodiments without losing the effect sought. For example, the preprocessing step 320 may be not necessary, or other selection conditions may be added between the preprocessing step and the analysis processing step. For example, a backup copy of the result of the preprocessing may be stored, and the result generated in any step of the processing may also be stored and backed up.

Figure 4:
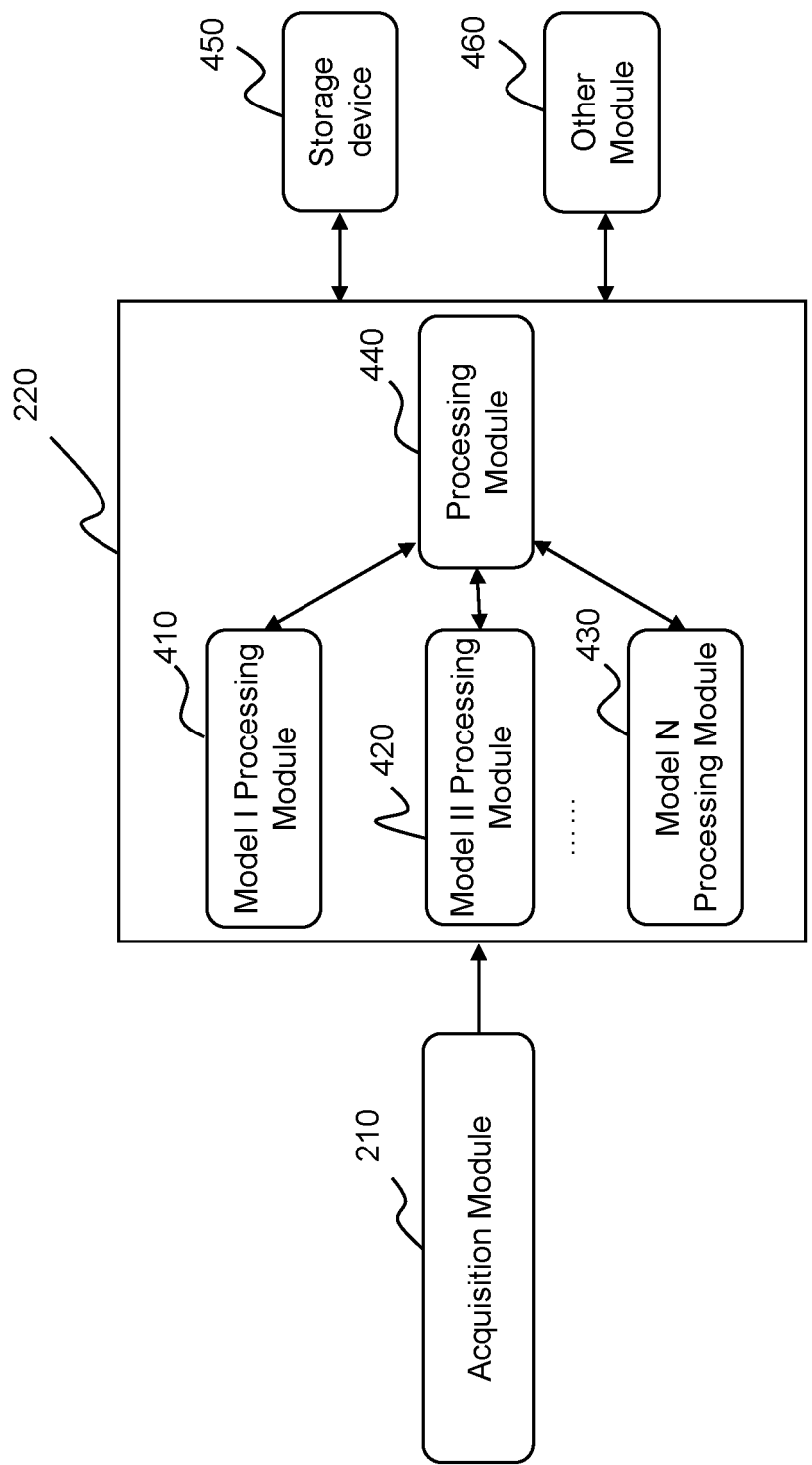
FIG. 4 is a schematic diagram of an analysis module according to some embodiments of the present disclosure.

FIG. 4 is a schematic diagram of the analysis module 220 and peripheral devices according to some embodiments of the present disclosure. The analysis module 220 may include a model I processing module 410, a model II processing module 420, a model N processing module 430, and a processing module 440. The analysis module 220 may be connected to a storage device 450 and an other module 460. The storage device 450 may be integrated in the analysis module 220, be integrated in the acquisition module 210, or be a standalone storage device. The analysis module 220 may be selectively connected to one or more acquisition modules 210, and/or be selectively connected to other modules. The aforementioned connections between all the modules or devices may be wired or wireless. The three model processing modules 410, 420, 430 and the processing module 440 within the analysis module 220 may be connected to one another, and/or connected to other modules separately. The connections between the modules are not limited to the ones illustrated in FIG. 4. The above descriptions of the processing modules are provided merely for illustrating purposes, and should not be considered as the only embodiment. Any module above may be implemented by one or more components. The functions of the modules are not limited within the scope of the present disclosure. Obviously, for persons having ordinary skills in the art, after understanding the principle of the analyzing process, without departing from the principle, may make any modification and variation in forms and details to the specific embodiments of the analyzing process, and may make any simple derivation and substitution. Without further efforts, the persons having ordinary skills in the art may make any modification or combination to the modules. However, these modifications and variations are still within the scope of the above descriptions. For example, the analysis module 220 may execute various functions. The analysis module 220 may determine whether there is noise in the acquired vital sign signals. Alternatively or additionally, the analysis module 220 may remove the noise from the acquired vital signs signals. The processing module 440 may not be necessary when the analysis module 220 merely executes the function of computing the physiological parameter. Similarly, the three model processing modules of the analysis module 220 may co-exist or may exist separately. When the analysis module 220 is operating, one or more modules of the plurality of processing modules may be selectively operated, the plurality of modules may be operated in phases, the plurality of modules may be operated simultaneously, or the model processing modules may be operated in combination in other time periods. Moreover, any one of the model processing modules may perform a computing process on the results from one or more other model processing modules, or simultaneously or not simultaneously transmit the results of different model processing modules to the processing module for processing.

All the data of vital sign signal may be selectively stored in the storage device 450 after being received, computed, analyzed, determined, and/or processed by the analysis module 220 so that the analysis module 220 may retrieve and analyze the data at any time during any of the following steps. The storage device 450 mentioned herein broadly refers to all media that may read and/or write information, such as but not limited to Random Access Memory (RAM) and Read Only Memory (ROM). Specifically, the storage device 450 may include various storage components such as hard disk, floppy disk, USB flash disk, and/or optical disk. The RAM may include but is not limited to decatron, selectron, delay line memory, Williams tube, dynamic random access memory (DRAM), static random access memory (SRAM), thyristor random access memory (T-RAM), zero capacitor random access memory (Z-RAM), or the like. The ROM may include but is not limited to bubble memory, twistor memory, thin film memory, magnetic plated wire memory, magnetic-core memory, magnetic drum memory, CD-ROM, hard disk, tape, early non-volatile random access memory (NVRAM), phase-change memory, magneto-resistive random access memory, ferroelectric random access memory, nonvolatile SRAM, flash memory, electrically erasable programmable read-only memory, erasable programmable read-only memory, programmable read-only memory, mask ROM, floating connected gate random access memory, Nano-RAM, racetrack memory, a variable resistive random access memory, programmable metallization unit, or the like. The above-mentioned storage devices are merely examples, and storage devices used in the system are not limited thereto.

Figure 5:
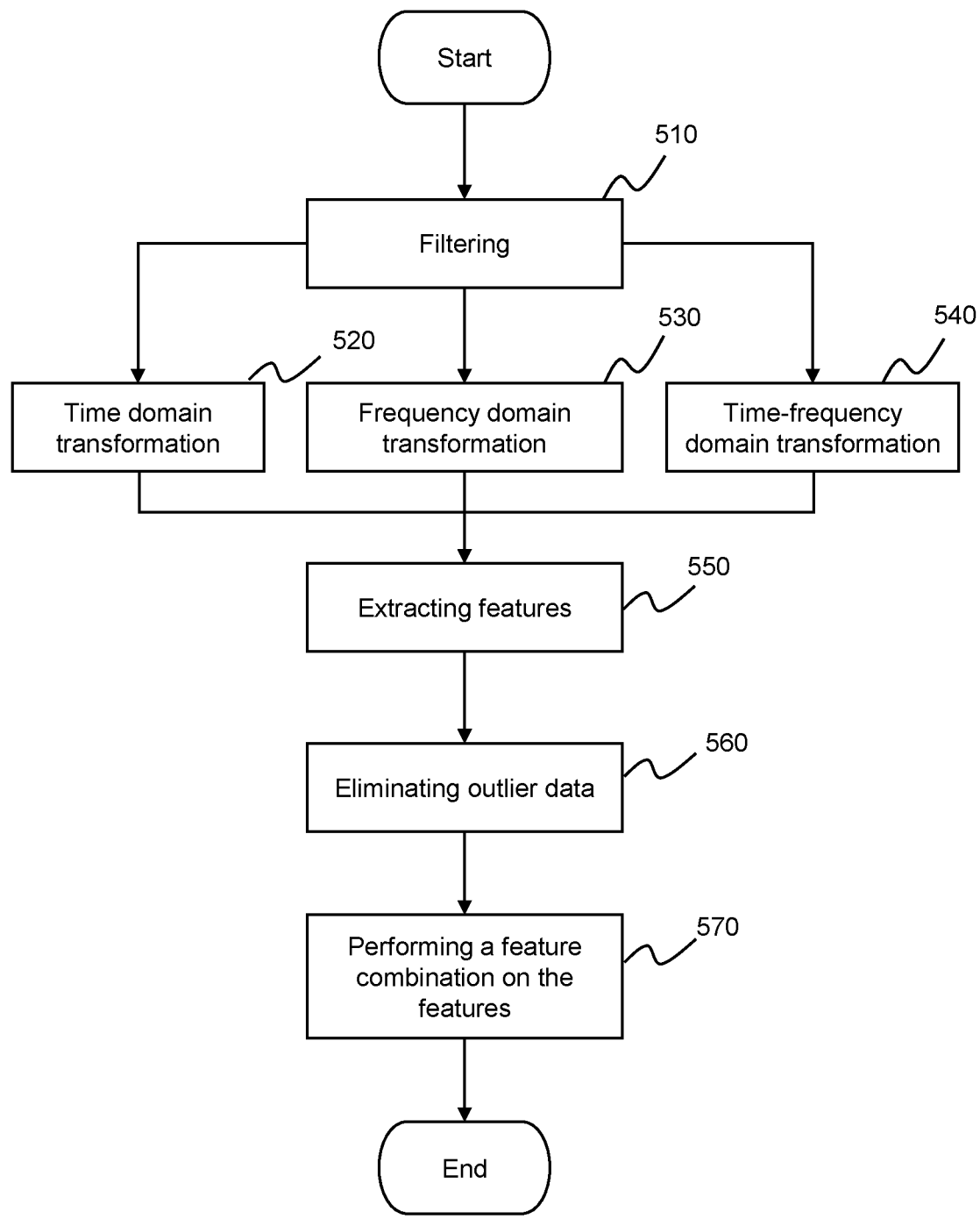
FIG. 5 is a flowchart illustrating an exemplary process of feature analysis of the vital sign signal according to some embodiments of the present disclosure.

FIG. 5 is a flowchart illustrating a process for extracting features from the vital sign signal by the analysis module 220 according to some embodiments of the present disclosure. The vital sign signal of a living body may be filtered in step 510. The filtering process may include removing noise from the vital sign signal. The noise may be caused by power interference, electric interference, or the like. In some embodiments, the noise may be detected by obtaining values of features (also referred to therein as feature value) of the vital sign signal and setting corresponding feature thresholds to determine whether there is noise in the information included. For example, by using a threshold crossing sample count (TCSC) algorithm, a time delay algorithm (TDA), and/or a kurtosis computation, a plurality of feature values may be obtained respectively. By setting thresholds for the obtained feature values, the existence of noise may be analyzed and determined. The vital sign signal including noise may be processed through the corresponding filtering process. In some embodiments, the segments of the vital sign signal including noise may be discarded. In some other embodiments, the vital sign signal including noise may be processed through a corresponding filtering process to remove the noise. Specific processing approach(s) may include but is not limited to a low-pass filtering, a band-pass filtering, a wavelet transform filtering, a median filtering, a morphological filtering, a curve fitting, or the like. After the noise is analyzed and filtered in step 510, the filtering result may be outputted via the output module 230.

In step 520, the operation of a time domain transformation may be performed on the vital sign signal to obtain the representation of the vital sign signal at different time points. The operation may include translation, convolution, computing a product with a specific kernel function, scale transformation, operating a specific function on the vital sign signal, or any combination thereof. The specific function operated on the vital sign signal may be a linear function. In some other embodiments, the specific function operated on the vital sign signal may be a non-linear function, such as a polynomial function, a function in an exponential form, a logarithmic function, a trigonometric function, a rational function, or any combination thereof.

In step 530, the operation of a frequency domain transformation may be performed on the vital sign signal to obtain the representation of the vital sign signal in frequency domain. The frequency domain transformation may include Fourier transform, fast Fourier transform (FFT), translation in frequency domain, convolution, computing a product with a specific kernel function, a scale transformation, operating a specific function on the vital function signal, or any combination thereof. The specific function operated on the frequency domain signal may be a linear function. In some other embodiments, the specific function operated on the vital sign signal may be a non-linear function, such as a polynomial function, a function in an exponential form, a logarithmic function, a trigonometric function, a rational function, or any combination thereof.

In step 540, the operation of a time-frequency domain transformation may be performed on the vital sign signal to obtain the representation of the vital sign signal in the time-frequency domain. The time-domain transformation may include wavelet transform, multi-windows time-space transform, translation in time-frequency domain, convolution, computing a product with a specific kernel function, scale transformation, operating a specific function operations on the time-frequency domain signal, or any combination thereof. The specific function performed on the time frequency domain signal may be a linear function. In some other embodiments, the specific function performed on the vital sign signal may be a non-linear function, such as a polynomial function, a function in an exponential form, a logarithmic function, a trigonometric function, a rational function, or any combination thereof.

In step 550, a time-domain signal, a frequency-domain signal, and a time-frequency-domain signal generated in the above steps 520, 530, 540 may be inputted into the analysis module 220 for feature extraction. The features may include various parameters of the time-domain signal, the frequency-domain signal, and the time-frequency-domain signal, such as time parameters, frequency-domain parameters, video parameters, amplitude parameters, area parameters. The features may also include composite features formed by performing a feature combination on given features. In some embodiments, the feature combination may be a linear combination. In some other embodiments, the feature combination may be non-linear, such as a polynomial combination, a combination in an exponential form, a logarithmic combination, a trigonometric combination, a rational combination, or any combination thereof.

In step 560, outlier data in the extracted features may be detected and eliminated.

In step 570, the features obtained after the outlier data is eliminated may be used to generate composite features via a feature combination. In some embodiments, the feature combination may be a linear combination. In some other embodiments, the feature combination may be non-linear, such as a polynomial combination, a combination in an exponential form, a logarithmic combination, a trigonometric combination, a rational combination, or any combination thereof. In some more specific embodiments, the feature combination for generating a composite features may adopt a dimension-reducing approach by, for example, using a threshold approach, a syntactic pattern recognition, a Gaussian function decomposition, a wavelet transform, an HTT algorithm, a linear discrimination analysis, a quadratic discriminant analysis, a maximum entropy classifier, a decision tree, a decision table, a kernel estimation, a nearest neighbor algorithm, a naive Bayes classifier, a neural network, perceptrons, a support vector machine, a gene expression programming, a hierarchical clustering, a k-means clustering, a correlation clustering, a kernel principal component analysis, a lifting methods, a Bayesian network, a Markov random field, a multi-linear principal component analysis, a Kalman filter, a particle filter, a Gaussian process regression, a linearity Regression or expansion, an independent component analysis, a principal component analysis, a conditional random domain, a hidden Markov model, a maximum entropy Markov model, a recursive neural network, a correlation rule, an inductive logic programming, a similarity measure learning, a deep neural network, a deep belief network, a convolutional neural networks, a deep convolutional belief networks, etc. The specific approach may be any one of the above algorithms or any combination of the above algorithms. The above approaches may be related directly or indirectly. The feature extraction described above may not be necessary. For persons having ordinary skills in the art, multiple variations and modifications may be made under the teachings of the present disclosure. However, those variations and modifications should not depart from the scope of the present disclosure.

Figure 6:
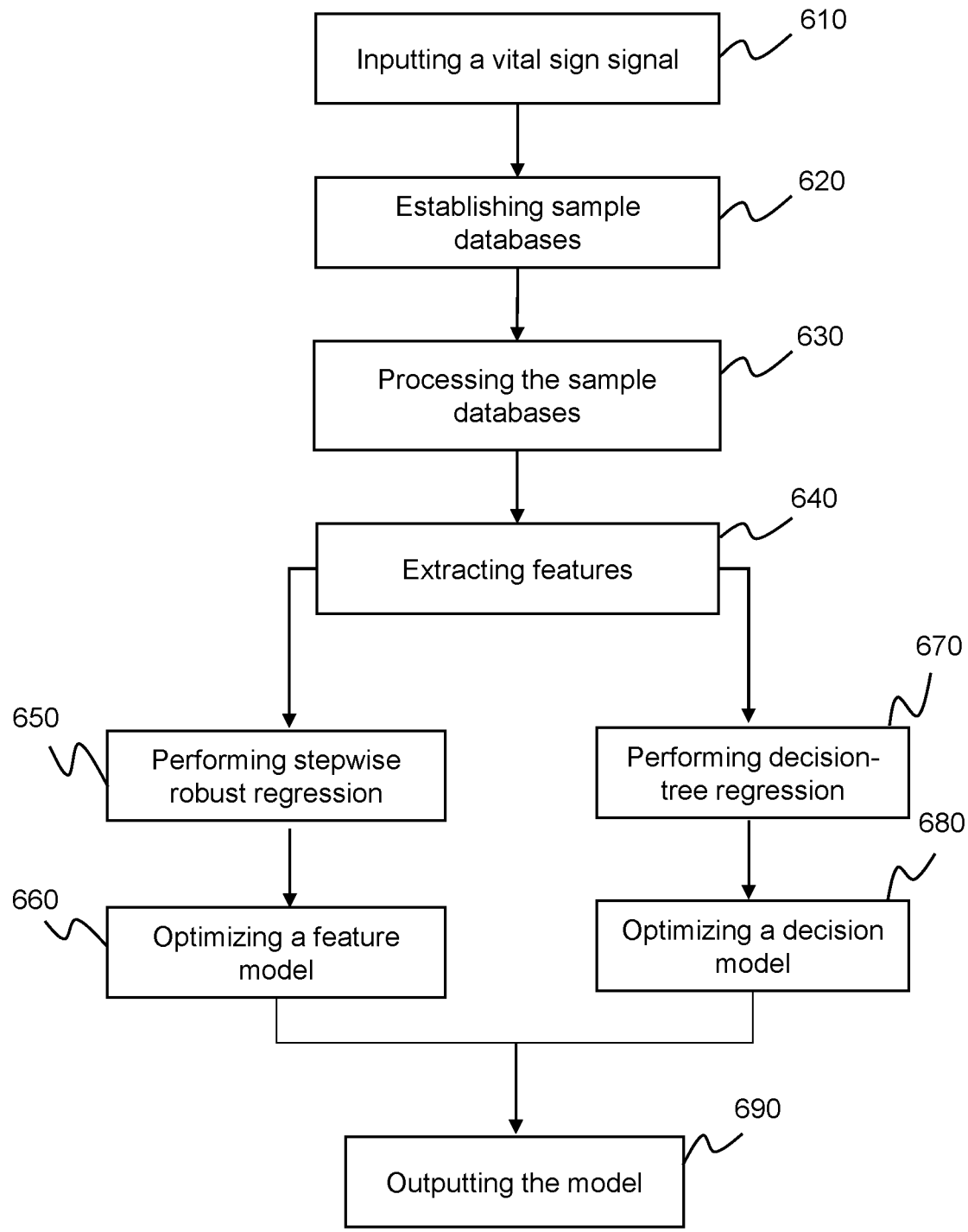
FIG. 6 is a flowchart illustrating a process for constructing a model and generating a decision model for different populations of the vital sign signal according to some embodiments of the present disclosure.

FIG. 6 is a flowchart illustrating a process of constructing a model library for different categories of the vital sign. Firstly, in step 610, sets of vital sign signals each of which satisfies a specific requirement may be inputted. In some embodiments, each of the inputted sets of vital sign signals satisfying the specific requirement may be a set of vital sign signals designated with a common tag. The vital sign signals may be pulse wave signals. The pulse wave signal may be obtained via a photoplethysmography measurement manner, or be obtained based on a pressure wave signal obtained by a pressure sensor. The tag of the vital sign signal may be "normal," "poor perfusion," "motion interference," "skin color," "gender," "age," "medical history," or any other tag for the populations to which the vital sign signals correspond. The tag of the vital sign signal may also correspond to behavior state/status of a certain population, such as "motion," "resting," "still," "sitting," "sleeping," "running," or the like. In some embodiments, the tag of the behavior status/status may have one or more sub-tags. For example, the tag "motion" may have sub-tags such as "short-term vigorous motion," "short-term slight motion," "long-term vigorous motion," "long-term slight motion," or the like. The set of the vital sign signals designated with a common tag may be extracted from different living bodies with a common tag. For example, a set of vital sign signals with a tag of "black skin color" may be a set of vital sign signals satisfying a specific requirement.

In step 620, sample databases may be established based on the inputted sets of vital signs signals. Sample databases of different tags (e.g., "normal," "poor perfusion," "venous overflow caused by motion interference," and different "skin color") may be established through designed different experiment schemes.

Subsequently, in step 630, the established sample databases may be processed. The processing may include: 1. acquiring sample data according to the experiment schemes and setting different tags for different sample data; 2. extracting data segments including valid data from the sample data and matching a reference value of the blood oxygen saturation with the extracted data segments; 3. eliminating outlier data, which may include error data inputted manually and identified error data related to device parameters, such as the data whose reference value is out of a trust range, identified error data relating to a signal feature point, etc.

In step 640, features may be extracted from the processed sample database. In some embodiments, the operation for extracting the features may be the operation related to feature extraction described in connection with FIG. 5. The extracted sets of features may be inputted to step 650 and step 670.

In step 650, stepwise robust regression may be performed on the extracted sets of features. Specifically, the operation may include classifying the extracted sets of the features, cleaning the invalid data, normalizing the data after cleaning, and performing computation of stepwise robust regression. Subsequently, a feature model may be optimized in step 660. In some embodiments, the optimizing the feature model may include determining an estimated value based on the Bayesian information criterion, determining variables of the model, a residual analysis, and normalizing coefficient threshold. Detailed description of optimizing the feature model may be found in the section about optimizing the feature model in PCT Application No. PCT/CN2017/094762, entitled "Systems and methods for determining blood pressure of a subject."

In step 670, a decision-making regression may be performed on the inputted set of features, and a decision model may be optimized in step 680. The decision model may be configured to determine a type of set to which the new sample data belongs. A weighted mean of a plurality of models may be designated as an output of the decision model. Values of the feature parameters may have different representations in different sample data, therefore, feature parameters (X) and data tag (Y) may be matched for modeling. In the optimization of the decision model, the fitting ability of a single tree may be reduced by suppressing the complexity of the decision tree, such as limiting the maximum depth of the tree, limiting the sample number of the leaf nodes, and limiting the minimum sample number for splitting a node. The generalization capability of the model may be optimized by integrating a plurality of decision trees. If there is a regression or classification error in a base leaner, the error may be corrected in a next round of base learning, and the decision model may be optimized by fitting residuals. The operation may be executed via some function packages of machine learning and statistical learning, such as gbm package in R Language. Finally, in step 690, a model corresponding to the vital sign signal satisfying the specific requirement may be outputted.

Figure 7:
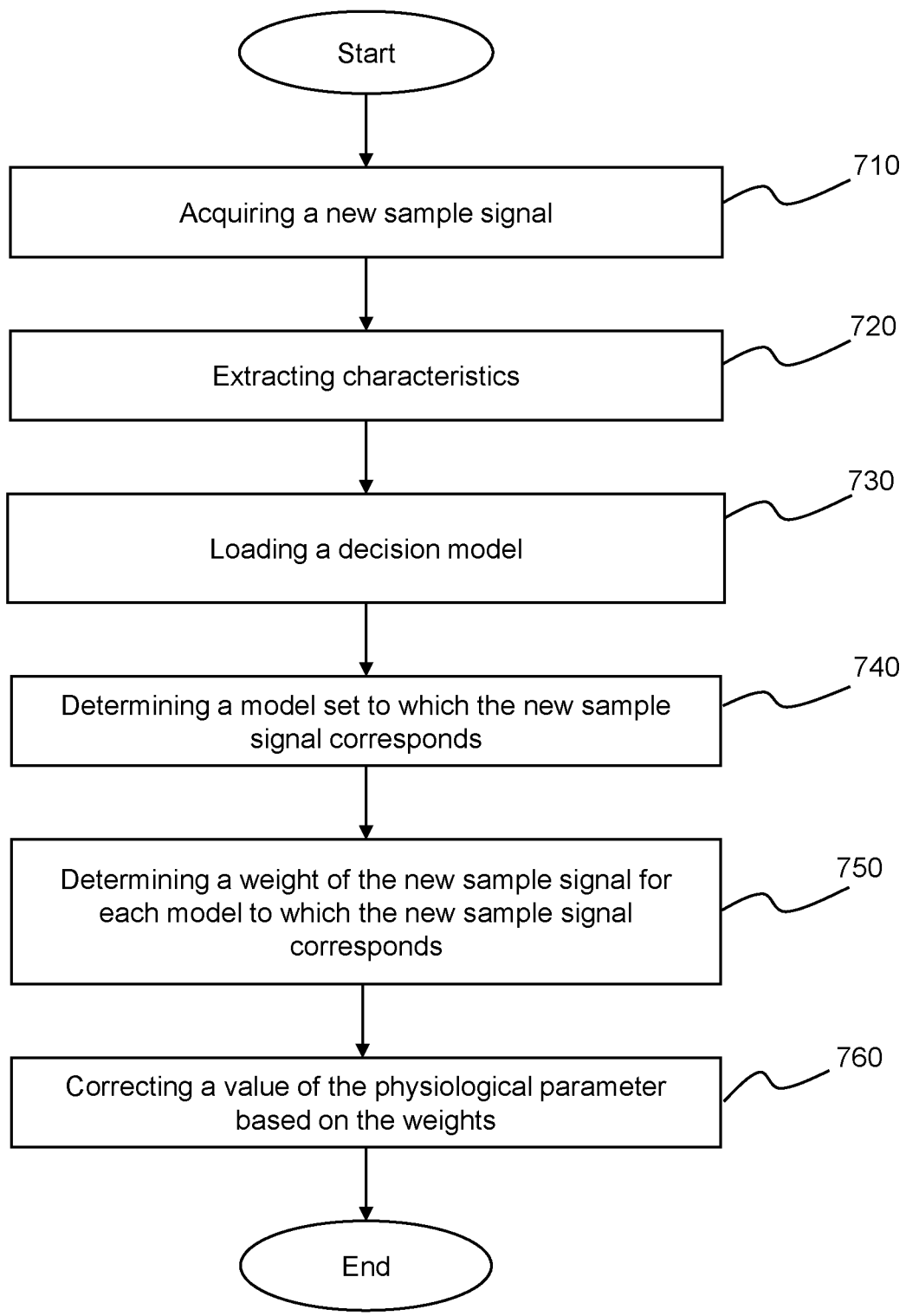
FIG. 7 is a flowchart illustrating a process for analyzing a physiological parameter of the vital sign signal according to some embodiments of the present disclosure.

FIG. 7 is a flowchart of determining a model to which the vital sign signal corresponds and correcting a physiological parameter of the vital sign signal. In some embodiments, the vital sign signal may be a PPG signal, and the physiological parameter of the vital sign signal may be blood oxygen saturation. Firstly, in step 710, an acquired vital sign signal may be inputted as a new sample (hereinafter also referred to as "new sample signal"). The vital sign signal may be a pulse wave signal. The pulse wave signal may be acquired via the PPG measurement manner, or obtained from a pressure wave signal acquired by a pressure sensor. The length of signal window applied to the vital sign signal may be related to physiological characteristics of the related individual.

In step 720, features of the inputted vital sign signal may be extracted. In some embodiments, the operation for extracting features may be the operation related to feature extraction described in connection with FIG. 5.

In step 730, a decision model may be loaded. The decision model may be used to classify the inputted vital sign signal and the corresponding features to determine the type of the vital sign signal. For example, the decision model may determine that the vital sign signal corresponds to "yellow skin color". In some embodiments, the classification of the vital sign signal may be a multi-classification. For example, the vital sign signal may be classified as corresponding to different types "yellow color skin," "female," "poor perfusion," and "motion interference". The decision model may be a perceptron or a multi-layer perceptron (MLP). In some embodiments, the decision model may include a decision tree model or a variant (e.g., gradient boosting decision tree (GBDT), gradient boosting regression tree (GBRT)) thereof, or the like. In step 740, the decision model may be used to determine a model set to which the new sample signal corresponds, so as to determine the model set to which the new sample signal corresponds. For example, with the decision model, it may be determined that the new sample signal corresponds to a model of "yellow skin color". As aforementioned, with the decision model, it may also be determined that the model to which the new sample signal corresponds is a multi-classification model. For example, the model to which the new sample signal corresponds may be a model of "yellow color skin," "female," "poor perfusion," and "motion interference".

In step 750, a weight of the new sample signal for each model to which the new sample signal corresponds may be determined. For example, the weight of the new sample signal for each model to which the new sample signal corresponds may be computed via a statistical distance between the new sample signal and each of the existing samples of the model to which the new sample signal corresponds. For example, the statistical distance between the new sample signal and the existing samples $s_1, s_2, \ldots, s_n$ of the model M may be defined as $L=(\|a-s_1\|+\|a-s_2$ ∥+ . . . +∥a−$s_n$∥)/n. The weight may be proportional to the statistical distance L between the new sample signal and the existing samples. For example, the weight w may be represented as w=cL, wherein the coefficient c may be a positive constant. The value of c may be based on the model. In some embodiments, the values of c for different models may be different.

After obtaining the weight of the new sample signal for each model to which the new sample signal corresponds in step 750, a value of the physiological parameter of the new sample signal may be modified based on the weights in step 760. In some embodiments, the physiological parameter of the new sample signal may be blood oxygen saturation. Specifically, each model $M_i$ to which the new sample signal corresponds may be used to compute a predicted value of the physiological parameter $e_i$, and the value of the weight of the new sample signal $w_i$ associated with the model $M_i$. The modification of the physiological parameter may be performed by:

$$(w_1 e_1 + w_2 e_2 + \ldots + w_n e_n)/(w_1 + w_2 + \ldots + w_n)$$

The embodiments described above only express several specific methods of implementation of the disclosure, and their descriptions are more specific and detailed, but they cannot be construed as limiting the scope of the disclosure. It should be noted that, for persons having ordinary skills in the art, without leaving the idea of this disclosure, a number of variants and improvements may be made, such as the new characteristic disclosed in this specification or any new combinations, and the steps or any new combinations of new methods disclosed, which shall fall within the scope of protection of this disclosure.

What is claimed is:

1. A method implemented on a computing device having one or more processors and one or more storage devices, the method comprising:
   acquiring, by an electronic device, a vital sign signal of an object, wherein the vital sign signal indicates a physiological parameter of the object detected by the electronic device;
   obtaining, by a processor, via a wired or wireless network, the vital sign signal;
   extracting, by the processor, features from the vital sign signal;
   loading, by the processor, a decision model;
   determining, by the processor, one or more sets of populations corresponding to the vital sign signal based on the decision model and the extracted features;
   obtaining, by the processor, one or more physiological parameter computing models established based on sample signals of the one or more sets of populations, wherein each of the one or more physiological parameter computing models corresponds to each of the one or more sets of populations;
   for the each of the one or more physiological parameter computing models, computing, by the processor, a weight relating to a statistic distance between the vital sign signal and each of at least some of the sample signals that are used to establish the physiological parameter computing model; and
   determining a value of the physiological parameter of the object based on the weights and the one or more physiological parameter computing models.

2. The method of claim 1, wherein the vital sign signal includes a pulse wave signal.

3. The method of claim 2, wherein the vital sign signal includes information of blood oxygen.

4. The method of claim 3, wherein the physiological parameter includes blood oxygen saturation.

5. The method of claim 4, wherein the one or more sets of populations are determined based on skin colors of the populations.

6. The method of claim 4, wherein the one or more sets of populations are determined based on a condition under which the sample signals of the one or more sets of populations are measured, and the condition for the measurement is poor perfusion.

7. The method of claim 4, wherein the one or more sets of populations are determined based on a condition under which the sample signals of the one or more sets of populations are measured, and the condition for the measurement is an existence of motion interference.

8. The method of claim 1, wherein the extracting, by the processor, features from the vital sign signal, includes performing at least one of a time domain transformation, a frequency domain transformation, and a time-frequency domain transformation on the vital sign signal.

9. The method of claim 1, wherein the decision model is a multi-classification model.

10. The method of claim 1, wherein the decision model is a perceptron or a multi-layer perceptron (MLP) model.

11. A system, comprising a storage device, wherein the storage device is configured to execute a plurality of sets of instructions for noise detection of a vital sign signal, and execute operations of:
    acquiring a vital sign signal of an object, wherein the vital sign signal indicates a physiological parameter of the object detected by an electronic device;
    obtaining, via a wired or wireless network, the vital sign signal;
    extracting features from the vital sign signal;
    loading a decision model;
    determining one or more sets of populations corresponding to the vital sign signal based on the decision model and the extracted features;
    obtaining one or more physiological parameter computing models established based on sample signals of the one or more sets of populations, wherein each of the one or more physiological parameter computing models corresponds to each of the one or more sets of populations;
    for each of the one or more physiological parameter computing models, computing a weight relating to a statistic distance between the vital sign signal and each of at least some of the sample signals that are used to establish the physiological parameter computing model; and
    determining a value of the physiological parameter of the object based on the weights and the one or more physiological parameter computing models.

12. The system of claim 11, wherein the vital sign signal includes a pulse wave signal.

13. The system of claim 12, wherein the vital sign signal includes information of blood oxygen.

14. The system of claim 13, wherein the physiological parameter includes a blood oxygen saturation.

15. The system of claim 14, wherein the one or more sets of populations are determined based on skin colors of the populations.

16. The system of claim 14, wherein the one or more sets of populations are determined based on a condition under which the sample signals of the one or more sets of populations are measured, and the condition for the measurement is poor perfusion.

17. The system of claim 14, wherein the one or more sets of populations are determined based on a condition under which the sample signals of the one or more sets of populations are measured, and the condition for the measurement is an existence of motion interference.

18. The system of claim 11, wherein the extracting, by the processor, features from the vital sign signal, includes performing at least one of a time domain transformation, a frequency domain transformation, or a time-frequency domain transformation on the vital sign signal.

19. The system of claim 11, wherein the decision model is a multi-classification model.

20. The system of claim 11, wherein the decision model is a perceptron or a multi-layer perceptron (MLP) model.

* * * * *